US008868161B2

(12) United States Patent
Thierman

(10) Patent No.: US 8,868,161 B2
(45) Date of Patent: Oct. 21, 2014

(54) DETECTION AND DISPLAY OF MEASURED SUBSURFACE DATA ONTO A SURFACE

(71) Applicant: Jonathan Thierman, Baltimore, MD (US)

(72) Inventor: Jonathan Thierman, Baltimore, MD (US)

(*) Notice: Subject to any disclaimer, the term of this patent is extended or adjusted under 35 U.S.C. 154(b) by 0 days.

(21) Appl. No.: 13/732,279

(22) Filed: Dec. 31, 2012

(65) Prior Publication Data

US 2014/0187966 A1     Jul. 3, 2014

Related U.S. Application Data

(63) Continuation-in-part of application No. 11/854,866, filed on Sep. 13, 2007, now Pat. No. 8,364,246.

(51) Int. Cl.
*A61B 6/00* (2006.01)
*A61B 5/00* (2006.01)

(52) U.S. Cl.
CPC ................................ *A61B 5/0059* (2013.01)
USPC ..................... 600/476; 600/407; 600/477

(58) Field of Classification Search
USPC ............................... 600/407, 476, 477
See application file for complete search history.

(56) References Cited

U.S. PATENT DOCUMENTS

| 2005/0059868 A1* | 3/2005 | Schurman | 600/323 |
| 2008/0154128 A1* | 6/2008 | Milner | 600/427 |
| 2009/0281402 A1* | 11/2009 | Chance | 600/328 |

* cited by examiner

*Primary Examiner* — Joel Lamprecht
(74) *Attorney, Agent, or Firm* — Intrinsic Law Corp.; Ibrahim M. Hallaj

(57) ABSTRACT

The present disclosure provides systems and methods for imaging and display of subsurface features of a region of interest such as a portion of a body of a patient. A first imaging portion of the system is used to cause an interaction of an imaging beam with an underlying feature of a region of interest. A retro-reflected or returned portion of said imaging beam is detected by a detector which then provides an output to control a display portion of the system for displaying an image corresponding to that which was detected. The system can be used for guiding or assisting clinical or industrial operations or for diagnosis of medical conditions and other uses within medicine, industry and others.

7 Claims, 5 Drawing Sheets

DETECTION AND DISPLAY OF MEASURED SUBSURFACE DATA ONTO A SURFACE

RELATED APPLICATIONS

The present application is a continuation in part and claims the benefit and priority of U.S. patent application Ser. No. 11/854,866, bearing the title "Compact Feature Location and Display System", filed on Sep. 13, 2007, which is hereby incorporated by reference.

TECHNICAL FIELD

The present disclosure relates to imaging and visualization of features below the surface of an opaque object, for example blood vessels in tissue, and specifically in some instances to non-invasive subsurface measurements and display of the same information onto the surface.

BACKGROUND

The human body is supplied by a complex network of blood vessels as part of the vascular system. The blood vessels are fluid conduits allowing for flow and distribution of blood throughout the body, and are generally arranged into arterial and venous sub-systems, which are themselves hierarchically arranged from larger ma supply vessels down to small capillary pathways. A primary function of the blood flowing through the vessels is to carry and distribute oxygen and other nutrients to the organs and tissue of the body. Another function of the blood is to collect waste products from the organs and tissue. Mechanically, the general organization of the vascular system is that of a hydraulic supply and return network with the heart providing the pumping and control to drive oxygenated blood to the organs and tissue in arteries, and to return blood from the organs and tissue in veins. Capillaries form the lowest functions on the hierarchy of vasculature, including the actual chemical (oxygen) exchange, and connect the arterial portion of the vascular network with the venous part of the vascular network.

As it carries oxygen, nutrients and waste products within the entire body, the vascular system has been recognized as a good vehicle for introducing drugs into the body, and as a good vehicle for extracting meaningful (blood) samples representative of the condition of the body. Since many primary vessels run slightly below the surface of the skin, they are accessible for procedures to introduce a substance into the blood or to extract a sample of blood from the vessels. For example, a common procedure is to introduce a drug or a fluid into the blood stream intravenously using an intravenous ("IV") line. Glucose and antibiotics are examples of things commonly injected into a patient's veins using an IV line. In practice, a medical professional inserts a needle through the skin and through one wall of a relatively large and accessible vein and the injected fluid is released into the vein through the IV needle under pressure. The converse (blood sampling) is used by pulling blood from a vein, or allowing the blood to flow out of the vein and into the needle, to draw a blood sample from a patient these procedures can be painful to people, as they involve sticking the patient with a needle. Also, inaccurate placement of a needle can lead to improper delivery of the drug or fluid, and can cause unwanted injury to vessels and tissue in the vicinity of vessels. It is therefore preferable that the needle be inserted accurately and hit its mark without undue retries. The present discussion of veins can where applicable be extended to other types of fluid vessels, for example, arteries, capillary vessels, etc.

One type of clinical procedure using the location of the appropriate vessels is the insertion of a central line, also called a central venous catheter ("CVC"). A central line is a catheter, or tube, which is inserted into a vein and physically passed through the vein to the thoracic (chest) portion of the vena cava or the right atrium of the heart. The vena cava is a large vein delivering blood to the heart. Again, proper administration of a CVC benefits from knowledge of the location of the vessels of interest.

It is therefore useful to develop methods and systems for accurate location and imaging and detection of vessels, especially to assist in medical diagnoses and procedures that employ the blood vessels such as in the applications mentioned above. It would be especially useful to overcome present limitations and provide systems that combine accuracy, clinical relevance, comfort, and at the same time are relatively inexpensive, reliable, and not excessively cumbersome. This disclosure addresses some or all of these issues.

SUMMARY

The present disclosure relates to visualization of things and features within objects. Generally, for example, the measurement of data beneath a surface, and then the display or projection of the measurements onto the surface. This can include in some examples subsurface temperature maps, blood vessels, oxygen or other gas content beneath the skin and so on. In an example, this includes visualizing fluid conduits within solid objects or visualizing blood vessels (veins and/or arteries) within human bodies. In some respects the disclosure relates to the operation of the vascular system, e.g. in humans, but also in other animals, specifically addressing aspects of the imaging, detection and treatment of a patient condition by way of the vascular system. Existing systems that attempt to do so are excessively cumbersome, costly, ineffective, and not portable enough to be effective for all applications.

The present disclosure provides systems and methods for imaging and display of features of a region of interest, for example but not limited to, a portion of a body of a patient. A first imaging portion of the system is used to cause an interaction of an imaging beam with an underlying feature of a region of interest. A reflected or returned portion of said imaging beam is detected by a detector which then provides an output to control a display portion of the system for displaying an image corresponding to that which was detected. The system can be used for guiding or assisting clinical operations or for diagnosis of medical conditions and other uses within medicine, industry and others.

One particular embodiment is directed to an imaging system for imaging a region of interest, including an imaging light source providing an imaging light beam including light in a first range of the electromagnetic spectrum, an incident portion of said imaging light being suitable for optical interaction with an underlying feature of said region of interest and suitable to provide a return portion of said icing light following an optical interaction of said imaging light beam with said underlying feature; a detector adapted and arranged to detect a magnitude of a characteristic of said return portion of said imaging light and adapted to provide an output signal corresponding to said magnitude; a display light source providing a display light beam including light in a second range of the electromagnetic spectrum, the display light beam being suitable for projecting an image onto a surface of said region of interest; a controller adapted and arranged to receive the output signal from said detector and provide a control signal to control a characteristic of said display light beam; and a scanner for scanning said imaging and display light beams across said region of interest.

Another particular embodiment is directed to a method for detecting and generating a visual representation of a feature beneath the surface of an object, including generating an imaging light beam; controllably scanning said imaging light beam across at least a portion of said surface; detecting a characteristic of a returned portion of said imaging light beam which has interacted with said feature beneath the surface of the object; generating a control signal corresponding to a characteristic of said returned portion of said imaging light beam; generating a display light beam and modulating a characteristic of said display light beam using said control signal; and controllably scanning said display light beam across at least said portion of said surface so as to visibly represent said feature on said surface of said object.

DETAILED DESCRIPTION

Figure 1:
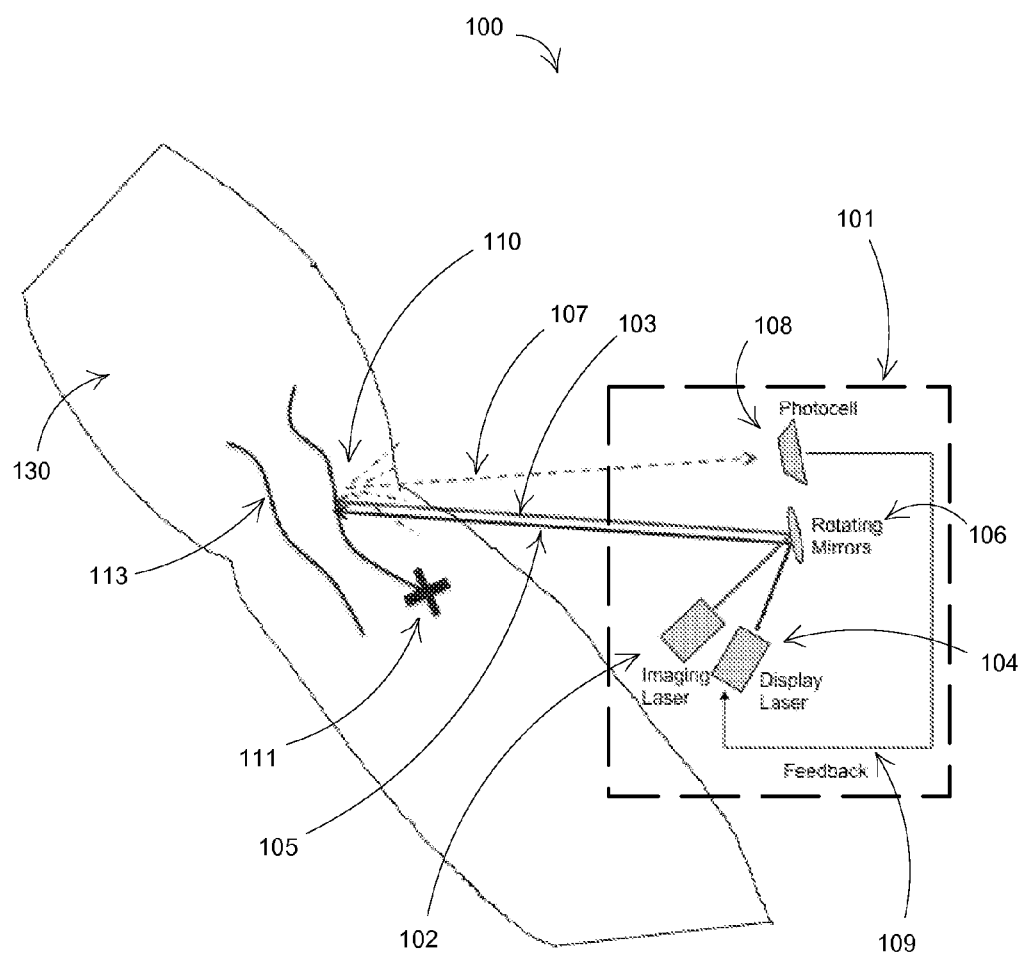
FIG. 1 illustrates an exemplary system for sensing and displaying subsurface blood vessel structure.

FIG. 1 illustrates an exemplary embodiment of a measurement and display system 100, which measures or detects some feature beneath a surface (e.g., skin surface) and displays information onto the surface indicative of the measurement. The system includes an imaging laser 102, which provides a coherent laser light output in an appropriate frequency range for imaging a feature beneath the surface, for example, the vascular system 113 in a patient's forearm 130. The system also includes a display laser 104, which provides a coherent laser light output in an appropriate frequency range for display of an image, typically in a visible range of the electromagnetic spectrum (i.e., having a wavelength between about 400 and 700 nm). The imaging laser 102 is generally used to obtain the location of the vessels of a patient, while the display laser 104 is generally used to indicate to a medical practitioner or user of the system 100 the location of the imaged vessels. In some embodiments, the location of the imaged vessels is substantially overlaid in a projection by display laser 104 onto the body of a patient so that the projected image of the vessels is outlined onto the surface of the patient's body (skin) and generally maps to the actual location of the vessels below the surface. In this way, a practitioner (surgeon, blood technician, emergency injection operator, etc.) can easily locate the vessels below the surface of the skin and access the vessels as necessary, with the desired accuracy, to accomplish their task. As will be explained below, the present system can also be used to detect and project information about temperature, oxygen content, and other measurable features.

One or more rotating mirrors 106 are used to direct the light output of the imaging and display lasers, 102 and 104 respectively, onto the desired location of the patient's body. Note that the rotating mirrors 106 can be augmented with other optical components such as other lenses, gratings, optical elements, apertures, gates, relays, mirrors, including flat, concave, convex, or combinations thereof to achieve the desired guidance of the light onto and collection of light from the patient's body. The illustration is intended to depict an optical assembly generally, including a combination of the above types of components or others as would be appreciated by those skilled in the art. This can include focusing or defocusing elements, filters, amplifiers, and other optical components as called for in a particular design of the system 100. The overall result of the one or more optical elements is an optical assembly that provides an imaging beam 103 by which the patient is irradiated and which is incident upon a region of interest ("ROI") 110 of the patient's body. One method of achieving the transmission of the incident beam over a rectangular ROI 110 on the skin is by means of a pair of mirrors which rotate in orthogonal planes and which redirect the laser beam in a controlled raster-scan pattern over an x and y coordinate axis projected onto the skin as will be described below. The imaging beam 103 operates on and interacts with the patient's vasculature and/or blood and provides the imaging of the vascular system in the ROT 110. In addition, the optical assembly (or a separate optical assembly if the aging and display paths are treated separately) carries a display beam 105 that is used to display the relevant image of the vascular system of the ROI 110. In some embodiments, the display beam 105 and imaging beam 103 propagate along parallel but spatially distinct optical paths. In other embodiments both the display and imaging beams 105, 103 propagate substantially along the same optical path and use shared optical components.

In operation, the imaging beam 103 is incident upon a ROT 110 on the patient's body as mentioned above. The light from the imaging beam 103 penetrates the patients skin and outer tissues so as to be incident on and interact with the patient's vascular system and/or the blood within the patient's vascular system in the ROI 110. The light from imaging beam 103 is then redirected, reflected, refracted, and otherwise sent upon its interaction with the patient's vascular system and/or blood in the ROI 110 back out from the patient's body in what we refer to herein as the "reflected imaging beam" 107. In one embodiment, near-infrared light is used which is known to have a higher absorption coefficient by blood than by other tissue. It should be appreciated that while reflection and absorption is one way of forming the reflected imaging beam 107, other optical and electromagnetic, chemical, and mechanical effects influencing the incident imaging beam 103 can also contribute to or influence the light forming the reflected imaging beam 107. The intensity of the reflected beam is a function of the absorption and scattering of the incident beam by the tissue and blood upon which it is incident at each location in the ROI as the incident beam is controllably scanned across the ROI.

The reflected imaging beam 107 is sensed by a photocell 108. More specifically, light forming the reflected imaging beam 107 is collected by some optical assembly that can include a lens, collator, filter, modulator, mirror, prism shaped collector, and other optical elements for delivery to a photocell 108, directly or indirectly. The photocell 108 can be of a number of sizes and configurations so that it can sense an intensity, power, amplitude, or other quantifiable characteristic of the reflected imaging beam 107. Photocell 108 may include an array or grid of photo-sensitive elements, e.g. arranged in two dimensions such as x-y Cartesian dimensions to form an output signal 109. When measured by a photodetector as a function of time (which can be directly related to the position of the incident beam in the ROI as it is scanned across the region), the signal intensity from the reflected beam can be used to recreate a map of the tissue reflection and absorption as a function of location in the ROI. Note that in some embodiments, the use of a line-source or spot/pencil beam source of light can be accomplished where the line or pencil beam sources are scanned with a mechanical or opto-electro-mechanical scanner so as to cover the surface of the ROI by translating the location of the spot or line beam over the surface of the ROI.

In turn, the photocell output 109 includes one or more signals that can be used to modulate the display laser 104 and hence modulate display beam 105. It can now be seen that the display portion of the system 100 is modulated by the imaging portion of the system 100 such that the images projected by the display portion of the system 100 can include information derived from the imaging portion of the system 100. In particular, in some embodiments, the display portion of the system 100 can be made to project an image of or light information representative of the blood vessels in the ROI 110. Even more particularly, a visible light image can be projected onto the surface of the patient's body that is effectively a representation that is spatially and visually matched to or corresponding to the blood vasculature beneath the ski in the ROI 110, where a light-coded portion of the projected image corresponds to an underlying vessel located directly beneath the light-coded portion of the projected image.

In one embodiment, the intensity of the projected display light beam 105 is modulated to spatially indicate on the patient's body in the ROI 110 the location of an underlying vein (or vessel that is to be injected or otherwise used in a medical procedure such as insertion of an IV line. In another embodiment, the inverse image (the negative) is possible, where the path and location of a blood vessel is darkened relative to the surrounding portion of the ROI 110. In yet another embodiment, a color-coding is used in a multi-color modulated display system to indicate various features of the vascular system being imaged. For example, characteristics of the vascular system including temperature, flow rate, oxygen level diameter, pressure, proximity to the surface, and other characteristics of the vessels and vascular network can be indicated by proper modulation of the imaging portion of the system 100.

As to the design of the rotating mirror assembly 106, this allows single line or planar scanning of a region of interest over a finite surface of the patient's body so that a single and relatively simple laser can be used for the imaging laser 102. In the same way, a relatively simple source can be used for the display laser 104 so that it can be used to cover and illuminate and form a projection onto a finite area of the ROI 110 of the patient's body. The operation of the rotating mirror can be controlled so that its speed of rotation allows a pulsed or continuous application of the laser sources 102, 104, to achieve a controlled result on the patient's body in the ROI 110. In one embodiment, the image and display lasers use the same rotating mirror assembly to minimize the number of parts and to ensure perfect collocation of the two laser beams on the ROI.

The display laser 102 itself can also be made of one or more parts so as to project an image (e.g., a two-dimensional image) or representation upon the patient's body's ROI 110. The display portion of the system 100 can be specifically built to include a microdisplay, digital projection elements, microreflectors, etc. that are controllable and addressable to form two-dimensional light output in display beam 105 that is indicative of the vascular structure being imaged. The modulation of the display portion of the system 100 can be amplitude modulation with a resulting dark-to-bright modulation of specific areas of the illuminated image corresponding to characteristics of the vascular system in the patient's body in the ROI 110.

In some embodiments, the system may comprise a low-power and hand-held apparatus within a compact housing 101. This application can be used in the field for military (e.g., combat) or civilian (e.g., emergency services) operations to locate blood vessels below the surface of a patient's skin under various conditions.

The system 100 can be portable, light-weight and powered by a DC power source such as a battery. A visible projected cross hair marker 111 or other marking can indicate to a user a location of interest on the surface of the skin (or other surface). For example, this marker can be projected on a location of a vein for the purpose of inserting a needle or catheter at this location of interest.

A region of interest ROI 110 can be a substantially two-dimensional surface of a patient's body having any of several shapes and sizes. For example, ROI 110 can extend in two Cartesian dimensions along the surface of a patient's body or skin, covering a substantially rectangular patch or aperture of said body or skin. Also, ROI 110 can extend in other coordinate systems such as a cylindrical or polar coordinate system and cover a substantially circular patch or aperture of said body or skin. Of course, in a real body, the surface covered by the ROI 110 can be generally planar (e.g., covering a small region of a human's abdomen) or can be non-planar and including topology that follows the surface of the body.

In some applications, the present system can be used to determine spatial profiles of thermal or chemical composition maps beneath a surface, e.g., the surface of a patient's skin. The information measured can be illustratively depicted or processed then displayed onto the surface, typically in a visible depiction overlaid over the region where the measurement itself is made.

One such application specifically would be for oximetry. As described above, blood provides a measurable medium due to the mechanical, optical and chemical composition thereof, and due to the contrast between the composition and nature of blood (including hemoglobin) and surrounding tissue. Oximetry measurements can be made based on infrared and red light wavelength absorption characteristics of oxygenated hemoglobin in the blood and/or deoxygenated hemoglobin in the blood. Deoxygenated hemoglobin absorbs red wavelengths (600-750 nm) more than oxygenated hemoglobin or other tissues. Oxygenated hemoglobin absorbs infrared wavelengths (850-1000 nm) more than other substances do. The ratio of infrared to red absorption in arterial blood correlates to the ratio of oxygenated to deoxygenated hemoglobin. In practice, these measurements can be used with lookup tables to determine an oxygen saturation or relative oxygenation level of the blood. This effect may be due to the chemical, mechanical, optical, electro-optical or other physical characteristics of the blood, and is intended here as an illustrative example of the present concept rather than a limiting discussion of the same. Those skilled in the art may appreciate the generalization of the instant description to similar or analogous uses in such or other materials in living or non-living organisms and subjects.

Figure 2:
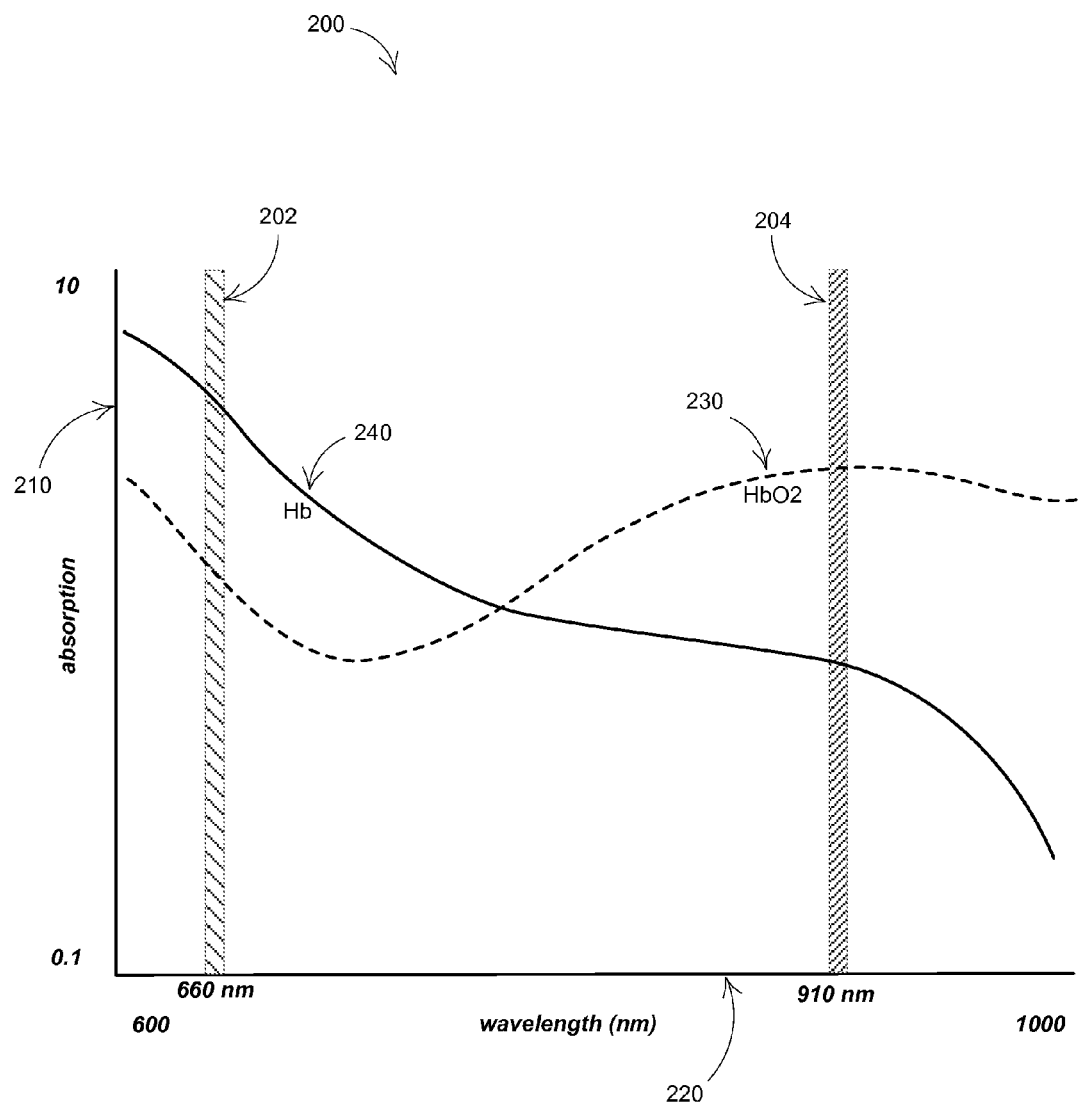
FIG. 2 illustrates an exemplary response curve for oxygenated and non-oxygenated blood as a function of wavelength of incident light.

FIG. 2 illustrates a simplified plot 200 showing absorption 210 as a function of wavelength 220. The exemplary absorption characteristics of oxygenated hemoglobin (HbO2) 230 compared to deoxygenated hemoglobin (Hb) 240 illustrate how quantitative determinations can be made for detecting vessels carrying Hb and HbO2 beneath the skin. For example, a wavelength 202 of 660 nm would be suitable for determining the presence of Hb while a wavelength 204 of 910 nm would be suitable for determining the presence of HbO2. Our imaging wavelength can detect one or both of these and our display wavelength can project a graphical representation of the vasculature on the surface of the skin substantially congruent to the physical location at which each of these things has been detected. Furthermore, a quantitative representation can be made so that the projected or displayed information shows the oxygenation level where this quantity has been measured. The amount of oxygen can be shown by a color coded projection or by projection of characters (e.g., numbers) onto the surface of the skin of the patient showing the same. In an example, the wavelength interacting with Hb is between 500 and 800 nm, optimally about 660 nm and a second wavelength interacting with HbO2 is between 800 and 1100 nm, optimally about 910 nm.

In an aspect, a combined laser path imaging system as described herein can be used to measure the ratio of absorption of infrared and red laser light at given locations in a region of interest, for example, on a point-by-point basis. The region of interest can be an antecubital fossa where several large blood vessels are present. Current vessel location systems require contact measurement apparatus, typically using the transmission of LED light in two selected wavelengths to calculate the oxygen saturation. However, the present system allows for a multi-wavelength compact (and sometimes portable or even hand held) device that can operate without contact to efficiently locate and display features below the skin surface. Again, this system and technique can be generalized to other surfaces such as walls or objects concealing subsurface features.

Figure 3:
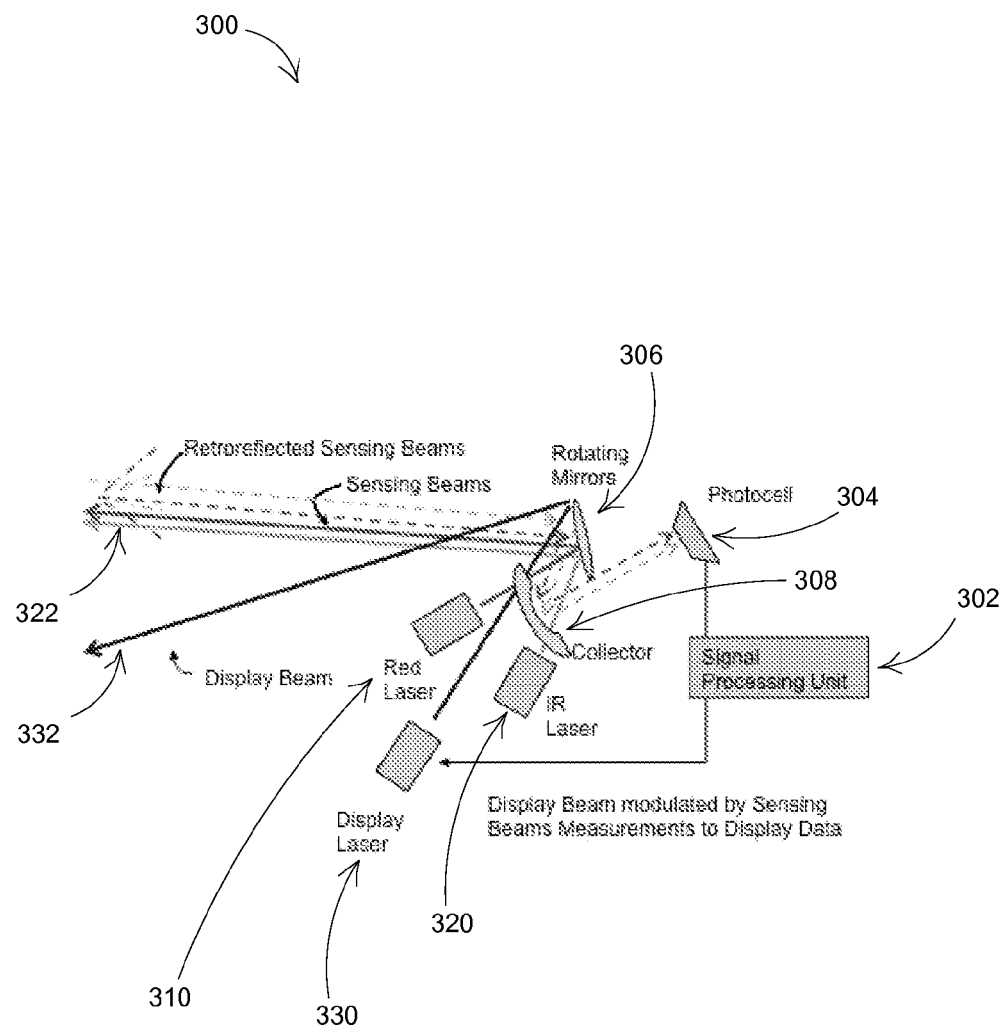
FIGS. 3 and 4 illustrate yet other exemplary systems for subsurface feature sensing and display.

FIG. 3 illustrates an exemplary system 300 for detecting and displaying measurements relating to a subsurface characteristic such as blood oxygenation information (oxymetry), which can be used to determine the state of hemoglobin as a function of location in a region of interest. This information can be of clinical value and can be used in imaging or other diagnostic and therapeutic procedures.

In this and other embodiments, computer technology, generally including processing hardware, software, firmware or other machine-readable instructions can be utilized to control the operation of the system. Those skilled in the art will understand various implementations of the present system that include such processing hardware and program instructions, some or all of which can be procured from components known in the art, but which are creatively now coupled and programmed and arranged as presently described. Uses of such technology can be made in the user interface designs for the present systems. For example, to allow entry of information and other desired settings and configurations of the system. Then, to allow for reading or receiving output from the system as needed. Interfacing the system to other machines is contemplated, including connecting the system through appropriate connectors and interface units to computer data networks, database systems, healthcare provider computer networks, insurance data systems, and other processing systems and networks. In addition, signal processing and data acquisition and filtering and related operations can be achieved through similar computerized functionality as would be known to those skilled in the art in view of the present disclosure. Hence, generally, a signal processing unit 302 is provided to achieve the above functions. Note that this functionality can be contained in a single general purpose or special purpose hardware or computer chip or processing circuit, or it may be divided among a number of circuit components and processors that cooperatively achieve the same end.

The other elements of system 300 are similar to that described above. For example, a plurality of laser sources operating at respective wavelengths are provided for the present imaging and display functions, including to investigate the presence and location of oxygen rich and oxygen poor hemoglobin in blood vessels beneath the skin (using, e.g., red laser 310, display visible laser 330 and infra red (IR) laser 320). These laser beams 322 are scanned across a region of interest, the imaging (or sensing) beams of which penetrate the skin surface to investigate what lies below, but the display laser beam 332 scans over the corresponding skin locations to show the user where the items of interest lie beneath. As mentioned, rotating mirrors 306, which generally mean a scanning optical assembly, are provided to scan the beams across the region of interest. Collector 308 acts to collect light in the system and direct it to photocell 304. More than three beams of various wavelengths may be used to further detect or discriminate sensed objects beneath the surface of the skin if desired by extending the present concept.

Figure 4:
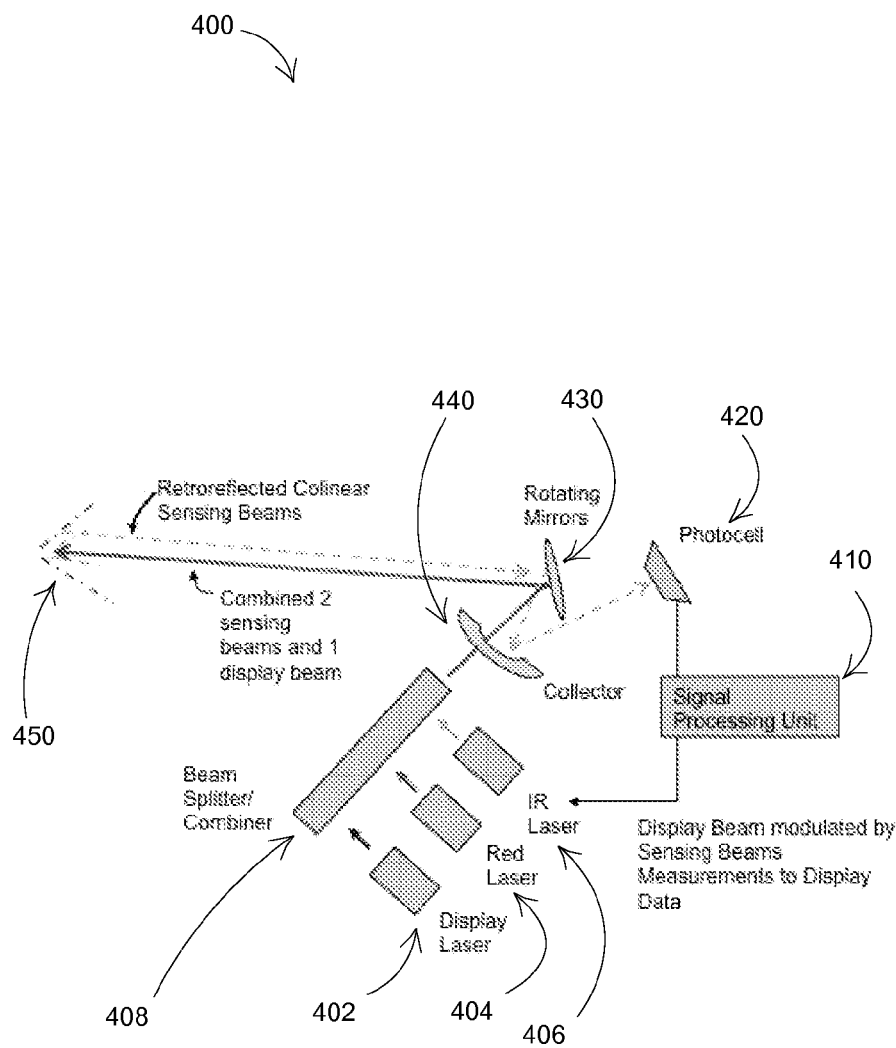

FIG. 4 illustrates another embodiment of a system 400 for detecting and displaying information based on sensing the same beneath the surface of an object but projecting the same onto the surface of the object. A plurality, e.g., three, laser beams are provided by respective sources 402, 404 and 406. The beams are directed by a common beam splitter or combiner 408 to pass through collector 440 onto rotating mirrors (or optical assembly) 430 and then to the region of interest 450. The rotating optical assembly 430 may be substituted with a solid state scanning or modulating assembly. In this embodiment the sensing (imaging) and display laser beams (from sources 404 and 402 respectively) are collinear and travel substantially along a common path or parallel pathway towards the region of interest 450. The scattered or retroreflected portion of the sensing beam returns to the rotating optical assembly 430 and is reflected at least in part by the collector 440 towards the photocell 420. Signal processing of the collected signal from photocell 420 is provided to signal processing unit 410 or other digital data units as discussed above.

In addition to that described previously, the present system can be used to accomplish pulse oximetry and improve the system's signal to noise ratio and eliminate or reduce background signals from the detected absorption signal. The system can be used to filter background absorption signals from the venous blood and other tissues. By tracking the time dependent absorption signal, the system can sense periodic peaks in absorption due to pulmonary pulsation of blood into the organ of interest. Periodic rise and fall of the intensity of the absorption signal can be used to define a DC absorption floor where background tissue and venous blood are responsible for the absorbed light rather than arterial blood. The system can then subtract the background absorption signal from the measured absorption signal to eliminate the noise of non-arterial blood absorption to yield a more accurate measurement of the arterial blood absorption characteristics in a location of interest. Pulse oximetry also permits measurement of heart rate as it affects the periodic flow of hemoglobin in the region of interest through measurements of the red and/or infrared absorption signals.

Figure 5:
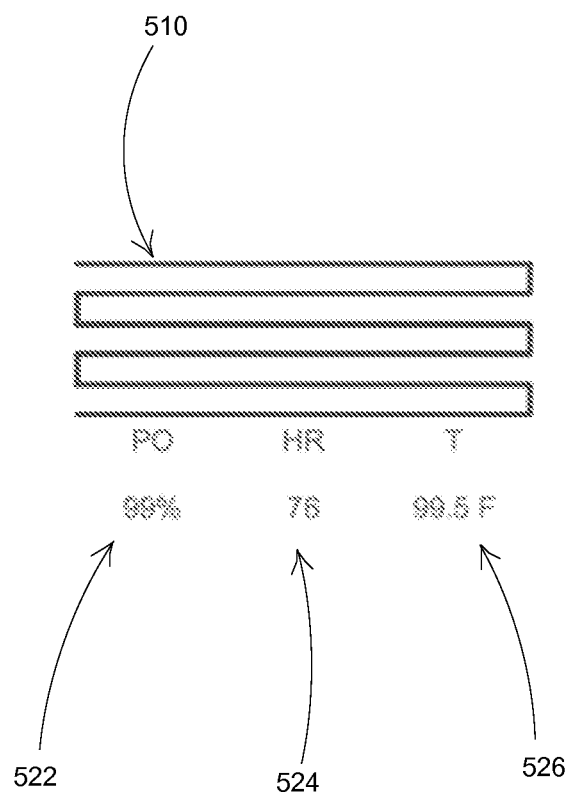
FIG. 5 illustrates an exemplary scanning pattern.

In another aspect, thermometry of tissues can be performed using the above system and techniques. Specifically, a temperature map as a function of space or space and time can be achieved. In fact, using the same architecture described herein, all of the above measurements and a display of the same can be made in a patient. FIG. 5 illustrates a simplified raster scanning pattern 510 over a region of interest (e.g., skin) providing pulse oximetry (PO) 522, heart rate (HR) 524 and temperature (T) 526 at each point in the region of interest.

It should be appreciated that the overall operation of the present imaging and display systems can be controlled by the construction of the system and by the method for applying the system to the patient's body. For example, the overall power and intensity of the imaging beam and the optical wavelengths used in the imaging portion of the system can affect the physical characteristics to which the system and imaging light responds. For example, using other wavelengths, e.g., infrared light, or near-infrared light, to image the body can provide deeper penetration into the body depending on the application and the type of tissue intervening between the light source and the feature being detected.

It should also be appreciated that the wavelength of the imaging and the display light beams do not have to be the same. For example, the imaging light may be in the infrared while the display light may be in the visible range of the electromagnetic spectrum, allowing plain-sight observation of the displayed image projected onto the ROI. Auxiliary features and functions can be microprocessor controlled and can include the ability to control the intensity of the imaging and the display portions of the system.

The present system and methods can be applied to more than just imaging of veins, arteries, and vessels in a human or animal body. But with proper selection of inking light source power and wavelength and system design the system can image piping and vessels and flow paths and other features hidden from view. For example, for inspection of circuit boards, fluid pipes, wear on parts, or other thermal or corrosive environments best imaged with ultraviolet ("UV") or infrared ("IR") or other light sources. A light source optimized in frequency and other characteristics to image the feature or object disposed below the skin or skin and subcutaneous fat layers or other tissue can be used.

In addition, there can be safety and architectural and manufacturing applications of the present systems and features. In addition to those already discussed such as IV and central line placement, some specific applications which the present system can be adapted for include: infrared ("IR") spectroscopy for chemical identification and blood analysis, for glucose and metabolic monitoring, for treatment of bleeding patients or those having internal bleeding, intraoperative use to avoid unwanted cutting of blood vessels during surgery, dermatological use for assessing ulcer vascularization and other possible uses of IR or UV signal from the skin to assess melanoma, differentiate malignant/benign, assess skin health from sun damage, deeper thermal imaging of sinuses in suspected sinusitis to assess for blood, visualizing varicosities and other telangiectasia of the venous system. In addition, the system could be adapted for use in biometric security applications such as personal identification and secure access applications where a unique or detectable blood vessel or pattern of blood vessels or other biometric characteristic is sensed and indicated.

Numerous other embodiments, modifications and extensions to the present disclosure are intended to be covered by the scope of the present inventions as claimed below. This includes implementation details and features that would be apparent to those skilled in the art upon review of the present disclosure and appreciation of the concepts and illustrative embodiments provided herein.

What is claimed is:

1. An imaging system for imaging a subsurface region of interest, comprising:
    a plurality of coherent light sources;
    an optical assembly that spatially scans respective outputs from said plurality of coherent light sources onto a surface of the region of interest;
    a first coherent light source providing light of a first wavelength of the electromagnetic spectrum that penetrates the surface to interact with a first kind of structure beneath said surface, a portion of said light at said first wavelength then returning to a detector of said light of said first wavelength;
    a second coherent light source providing infrared light at a second wavelength, longer than said first wavelength, said infrared light also penetrating the surface to interact with a second kind of structure beneath said surface, a portion of said infrared light then returning to a detector of said infrared light;
    a signal processing unit receiving a first signal corresponding to said returned portion of said first light and a receiving a second signal corresponding to said returned portion of said infrared light, said signal processing unit generating an output indicative of a sensed condition beneath said surface determined at least by both of said first and second signals received corresponding to the returned first light and returned infrared light; and
    a display light source emitting a visible display signal projected onto said surface of the region of interest corresponding to the sensed condition as a function of position on said surface of the region of interest.

2. The system of claim 1, said first light of first wavelength corresponding to light in the red portion of the electromagnetic spectrum.

3. The system of claim 1, said plurality of coherent light sources comprising laser light sources including at least two such sources providing respective wavelengths that are absorbed by oxygenated hemoglobin (HbO2) and non-oxygenated hemoglobin (Hb), respectively.

4. The system of claim 3, said first wavelength being absorbed by non-oxygenated hemoglobin (Hb) and having a wavelength between 500 and 800 nm.

5. The system of claim 3, said infrared wavelength being absorbed by oxygenated hemoglobin (HbO2) and having a wavelength between 800 and 1100 nm.

6. The system of claim 1, further comprising non-transitory computer readable medium for generating pulsed outputs of said first light wavelength and said infrared wavelength so as to reduce or cancel background noise artifacts to improve signal to noise output.

7. The system of claim 1, further comprising non-transitory computer readable medium for outputting readable characters indicating any of: percent oxygenation of a patient's blood, patient's heart rate and a temperature map of the patient's region of interest.

* * * * *